(12) United States Patent
Stopek et al.

(10) Patent No.: US 9,592,043 B2
(45) Date of Patent: Mar. 14, 2017

(54) MULTIZONE IMPLANTS

(75) Inventors: Joshua Stopek, Yalesville, CT (US); Jonathan D. Thomas, New Haven, CT (US)

(73) Assignee: Covidien LP, Mansfield, MA (US)

( * ) Notice: Subject to any disclaimer, the term of this patent is extended or adjusted under 35 U.S.C. 154(b) by 1610 days.

(21) Appl. No.: 12/721,937

(22) Filed: Mar. 11, 2010

(65) Prior Publication Data
US 2010/0249838 A1 Sep. 30, 2010

Related U.S. Application Data

(60) Provisional application No. 61/165,057, filed on Mar. 31, 2009.

(51) Int. Cl.
*A61B 17/04* (2006.01)
*A61B 17/00* (2006.01)

(52) U.S. Cl.
CPC ...... *A61B 17/0401* (2013.01); *A61B 2017/00004* (2013.01); *A61F 2250/003* (2013.01)

(58) Field of Classification Search
CPC ......... A61B 17/0401; A61F 2210/0004; A61F 2250/003; A61F 2002/30032
USPC ....... 606/76–77, 298, 331; 623/23.58–23.59, 623/23.75
See application file for complete search history.

(56) References Cited

U.S. PATENT DOCUMENTS

| 4,130,639 | A | * | 12/1978 | Shalaby et al. | 514/169 |
|---|---|---|---|---|---|
| 5,342,395 | A | * | 8/1994 | Jarrett et al. | 606/219 |
| 6,013,853 | A | * | 1/2000 | Athanasiou et al. | 424/423 |
| 6,069,295 | A | * | 5/2000 | Leitao | 623/11.11 |
| 6,596,296 | B1 | | 7/2003 | Nelson et al. | |
| 6,626,950 | B2 | * | 9/2003 | Brown et al. | 623/23.72 |
| 7,517,362 | B2 | | 4/2009 | Shanley et al. | |
| 2001/0051833 | A1 | * | 12/2001 | Walter et al. | 623/23.58 |
| 2002/0183858 | A1 | | 12/2002 | Contiliano et al. | |
| 2003/0036801 | A1 | | 2/2003 | Schwartz et al. | |
| 2003/0220700 | A1 | | 11/2003 | Hammer et al. | |
| 2005/0064005 | A1 | | 3/2005 | Dinh et al. | |
| 2005/0090828 | A1 | * | 4/2005 | Alford | 606/73 |
| 2005/0267565 | A1 | * | 12/2005 | Dave et al. | 623/1.15 |
| 2005/0283229 | A1 | | 12/2005 | Dugan et al. | |
| 2006/0045903 | A1 | | 3/2006 | Kadiyala et al. | |
| 2006/0147489 | A1 | | 7/2006 | Shanley et al. | |
| 2007/0077272 | A1 | | 4/2007 | Li et al. | |
| 2007/0129755 | A1 | | 6/2007 | Abbott et al. | |
| 2008/0097620 | A1 | | 4/2008 | Venkatraman et al. | |
| 2009/0177229 | A1 | | 7/2009 | Gulotta | |

FOREIGN PATENT DOCUMENTS

EP 1867301 A1 12/2007
WO WO 93/15694 8/1993
(Continued)

OTHER PUBLICATIONS

European Search Report for EP 10 25 0632, date of completion is Jul. 26, 2010 (3 pages).
(Continued)

*Primary Examiner* — Eduardo C Robert
*Assistant Examiner* — Julianna N Harvey

(57) ABSTRACT

Medical devices having more than one degradation zone or degradation mechanism are used for orthopedic repair devices and soft tissue fixation devices.

15 Claims, 4 Drawing Sheets

(56) References Cited

FOREIGN PATENT DOCUMENTS

WO  WO 2004/017857    3/2004
WO  WO2007/051120 A2  5/2007
WO  WO 2008/034007    3/2008

OTHER PUBLICATIONS

European Search Report for Appln. No. 10250634.2-1269 dated Jun. 24, 2010.
European Search Report for corresponding EP 10 25 0633, date of completion is Jul. 22, 2010 (3 pages).

* cited by examiner

MULTIZONE IMPLANTS

CROSS-REFERENCE TO RELATED APPLICATIONS

This application claims the benefit of U.S. Provisional Application No. 61/165,057, filed Mar. 31, 2009, the entire contents of which are incorporated herein by reference.

TECHNICAL FIELD

The present disclosure relates to degradable implants, and more specifically, to medical devices having more than one degradation zone.

BACKGROUND OF RELATED ART

Orthopedic fixation devices, such as anchors used to approximate soft tissue to bone, are well known in the art. Suture anchors may have a variety of configurations and may be constructed from a variety of materials, including biodegradable and non biodegradable materials.

While current orthopedic fixation devices perform satisfactorily, improvements in the field are desired.

SUMMARY

A fixation device is described herein in which the fixation device comprises at least two homogeneous degradation zones. In some embodiments, the two homogeneous zones degrade at different rates. In other embodiments, the two homogeneous zones degrade by different mechanisms, wherein at least one of the homogenous zones may degrade by bulk erosion and at least one of the homogenous zones may degrade by surface erosion. The composition of the first degradation zone may be a different composition or of the same composition as the second degradation zone.

Implants of the present disclosure may comprise an interface between at least one homogeneous degradation zones. For example, the implant may comprise an interface between a first homogenous degradation zone and a second homogeneous degradation zone. In other embodiments, the implant may comprise at least one interphase. The interphase may be between a first homogeneous degradation zone and a second homogeneous degradation zone.

The fixation device may include materials selected from the group consisting of polyesters, polyester polyalkylene oxide copolymers, polyorthoesters, polyhydroxybutyrates, polyhydroxyalkanoates, polyanhydrides, polyamines, polycarbonates, copolymers and combinations thereof.

In certain embodiments, a first homogeneous degradation zone comprises more amorphous regions than the second homogeneous degradation zone. Similarly, the second homogeneous degradation zone may comprise more crystalline regions than the first homogeneous degradation zone. In another embodiment, at least one homogeneous degradation zone comprises a porous structure.

Fixation devices of the present disclosure may be selected from the group consisting of spinal fixation devices, fracture plates, wires, pins, screws, anchors, intramedullary devices, artificial ligaments, artificial tendons, and artificial meniscus.

The fixation devices may further comprise a bioactive agent or a polymer drug. More specifically, the degradation of at least one of the homogeneous degradation zones may correspond to an elution of a bioactive agent.

BRIEF DESCRIPTION OF DRAWINGS

The illustrative embodiments described herein will become more readily apparent from the following description, reference being made to the accompanying drawings in which.

DETAILED DESCRIPTION OF EMBODIMENTS

The present disclosure is directed to medical devices (implants), including but not limited to orthopedic fixation devices such as interference screws or bone anchors and soft tissue repair devices. The medical device includes at least two degradation zones. In some embodiments, at least two degradation zones are located at an exterior concentric portion and an interior concentric portion, respectively, of the implant and at least one degradation zone includes a bioactive agent. In another embodiment, the degradation zones are located at a distal portion and a proximal portion of the implant. In an alternate embodiment, the fixation device includes at least two homogeneous degradation zones. In other alternate embodiments, the implant includes at least two degradation zones wherein each zone has a different degradation mechanism. Implants of the present disclosure may be made from a variety of materials including biodegradable polymers, ceramics and metal alloys and combinations thereof.

The term "biodegradable" as used herein is defined to include both bioabsorbable and bioresorbable materials. By biodegradable, it is meant that the materials decompose, or lose structural integrity under body conditions (e.g., enzymatic degradation or hydrolysis) or are broken down (physically or chemically) under physiologic conditions in the body such that the degradation products are excretable or absorbable by the body.

In the description that follows, the term "proximal" means the portion of the device which is nearer to the user, while the term "distal" refers to the portion of the device which is further away from the user.

Figure 1A:
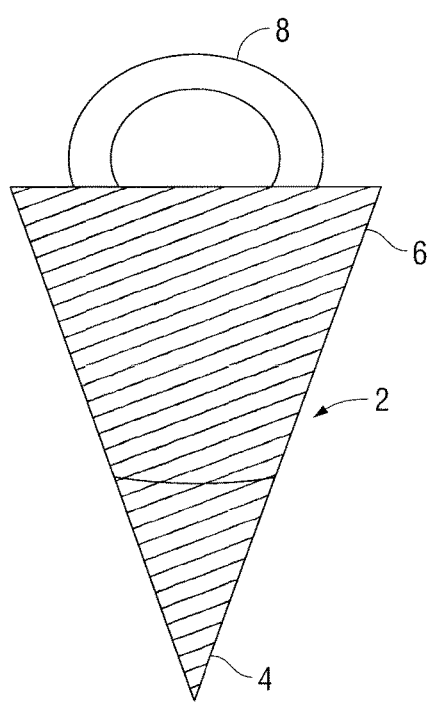
FIGS. 1A-1B show side views of embodiments of an implant having degradation zones according to the present disclosure.
Figure 1B:
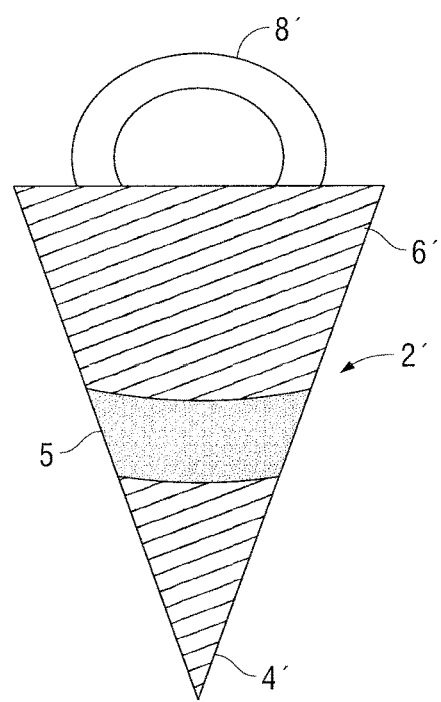

An implant according to one embodiment of the present disclosure is illustrated in FIGS. 1A and 1B. The bone anchor 2 comprises a conical elongate body including a distal portion 4 and a proximal portion 6. The bone anchor 2 also includes an external eyelet 8, located at the proximal portion 6 of the device 2. The bone anchor 2 is conical in shape, with the distal portion 4 forming an apex (sharp point). It is also envisioned that the distal portion 4 may be rounded, providing a blunt tip. In other embodiments, the distal portion 4 may be of any geometry or configuration which improves mechanical interlocking of the device with the surrounding tissue or bone. The external eyelet 8 is designed so as to communicate with a suture (not shown) such as an ultra high molecular weight polyethylene suture (UHMWPE).

In the illustrated embodiment, the distal portion 4 and the proximal portion 6 comprise materials with different degradation rates. More specifically, distal portion 4 of the device 2 may comprise materials and/or compositions having a faster degradation rate compared to the proximal portion 6 of the device. The proximal portion 6 of the device 2 may have a slower degradation rate, stabilizing the device 2 for a longer period of time, enabling more tissue ingrowth. It is also contemplated that the eyelet 8 may provide strength for a longer period of time (slowest degrading). In other words, the implant 2 degrades fastest at the distal portion 4 and slowest at the proximal portion 6. In alternate embodiments, the distal portion 4 and the proximal portion 6 may comprise different degradation mechanisms, e.g., surface erosion or bulk erosion, which will be discussed later. As shown, the implant 2 is threaded on the exterior, however it is envisioned that other embodiments may have different surface geometries including grooved, bumped, or flat which may improve mechanical stability of the device 2 with the surrounding tissue or bone.

It will be understood that FIG. 1B is a similar embodiment to FIG. 1A and therefore all numerals and descriptions which are the same are designated with the prime mark and the differences will be described below. FIG. 1B illustrates a bone anchor 2' which further includes an intermediate portion 5 located between the distal portion 4' and the proximal portion 6' of the implant 2'. The intermediate portion 5 may comprise materials and/or compositions which have a slower degradation rate than the distal portion 4', while exhibiting a faster degradation rate compared to the proximal portion 4' and the eyelet 8'. In general, the device according to FIG. 1B, would degrade fastest at the distal portion 4' and slowest at the proximal portion 6' of the implant 2' (similar to FIG. 1A).

Figures 2A, 2B:
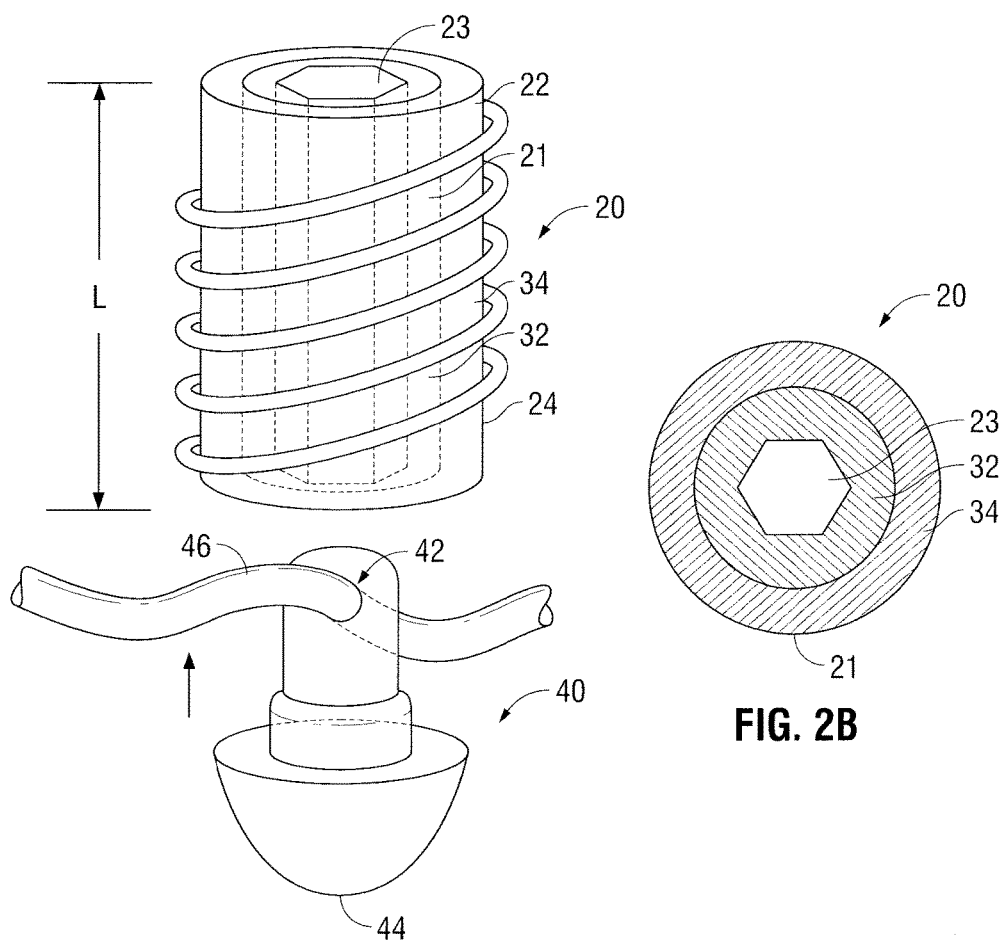
FIGS. 2A-2B show a side perspective view and a plan view of another embodiment of an implant according to the present disclosure.

Another embodiment of an implant according to the present disclosure is illustrated in FIGS. 2A and 2B. The implant 20 is a bone screw comprising a cylindrical elongate body 21 and an anchor pin 40. The elongate body 21 has a passageway 23 that extends axially therethrough. The elongate body 21 includes a proximal portion 22 which has a cavity for cooperating with a correspondingly-shaped external drive tool (e.g., Herculon™ Soft Tissue Fixation System, United States Surgical, North Haven, Conn.) for rotating the elongate body 21, and driving the elongate body 21 into a bone.

The bone screw 20 also includes concentric portions 32 and 34 (inner and outer degradation zones, respectively) which may extend the length of the entire circumference of the elongate body 21, although it is contemplated that at least one of the concentric portions (32, 34) may extend along a portion or arc of the circumference. As illustrated, the concentric portions 32, 34, are generally cylindrical or ring-shaped in cross-sectional area and extend along a length "L" of the elongate body 21, although it is contemplated that the concentric portions 32, 34, may extend a length which is less than the entire length "L" of the elongate body 21. The inner concentric portion 32 and outer concentric portion 34 are generally ring-shaped in cross-sectional area, although it is envisioned that the inner concentric portion 32 may be cylindrical in shape (the device comprising a generally core/sheath construct). In general, the inner concentric portion 32 is at least partially or substantially inside the outer concentric portion 34. In certain embodiments, the outer concentric portion 34 comprises the fastest degradation rate, while the inner concentric portion 32 comprises the slowest degradation rate. As shown, the implant 20 is threaded on the exterior of the elongate body 21, however it is envisioned that other embodiments may have different surface geometries including grooved, bumped, or flat which may improve mechanical fixation of the device with the surrounding tissue or bone. One embodiment of a bone screw which may be combined with the present disclosure is U.S. Pat. No. 5,156,616, which is incorporated by reference herein.

As the bone screw degrades, it allows for tissue ingrowth, enhancing the implant stability and integration. More specifically, as the outer concentric portion 34 degrades, allowing for tissue ingrowth, the inner concentric portion 32 stabilizes the device 20. Once the tissue ingrowth (into outer portion 34) mechanically supports the device, the inner concentric portion 32 may degrade, allowing further tissue ingrowth. In alternate embodiments, the concentric portions 32 and 34 may comprise different degradation mechanisms, e.g., surface erosion or bulk erosion, which will be later described. It is envisioned that the different degradation rates and/or mechanisms may be tailored by altering materials and/or compositions of the device, or altering various processing parameters.

The anchor pin 40 is in communication with a distal portion 24 of the elongate body 21 as indicated by the arrow in FIG. 2A. The anchor pin 40 includes an eyelet 42 at a proximal end and a rounded tip 44 at distal end. In embodiments, the eyelet 42 is in communication with a suture 46, such as, for example, an UHMWPE suture 46. When assembled for use, the anchor pin 40 is fed through the elongate body 21 and the suture 46 passes through the passageway 23 of the implant 20 and extends beyond the proximal portion 22 of the elongate body 21.

Figures 3A, 3B:
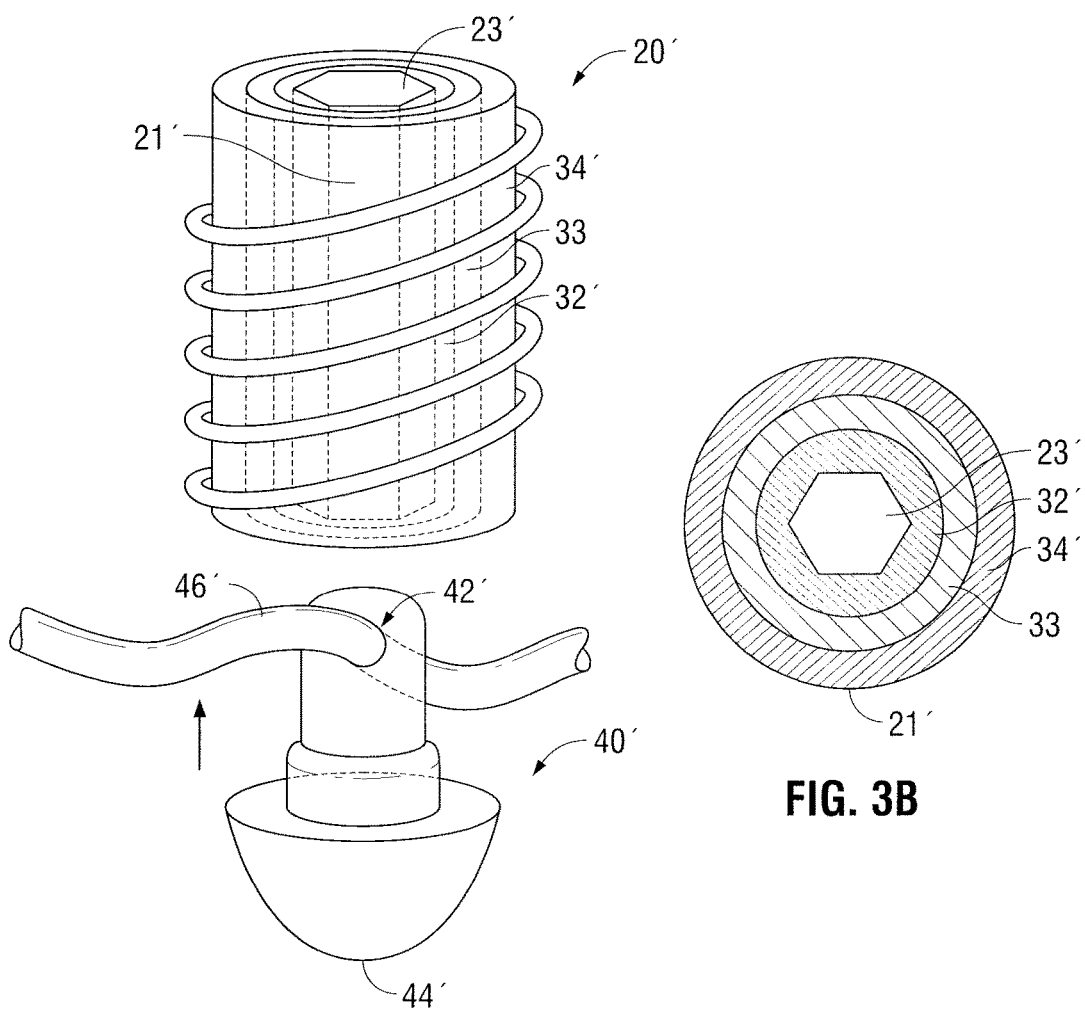
FIGS. 3A-3B show a side perspective view and a plan view of yet another embodiment of an implant according to the present disclosure.

It will be understood that FIGS. 3A-3B are similar embodiments to FIGS. 2A-2B and therefore all numerals and descriptions which are the same in FIGS. 3A-3B are designated with the prime mark and the differences will be described below. FIG. 3A illustrates a bone anchor 20' which further includes an intermediate concentric portion 33. The intermediate concentric portion 33 is generally ring-shaped in cross-sectional area, and is located between the outer concentric portion 34' and the inner concentric portion 32'. The intermediate concentric portion 33 may comprise materials and/or compositions which have a slower degradation rate than the outer concentric portion 34' while exhibiting a faster degradation rate compared to the inner concentric portion 32'. The device 20' degrades fastest at the outer concentric portion 34' and slowest at the inner concentric portion 32' of the implant 20'.

In another embodiment, the device includes at least two degradation zones, wherein at least one degradation zone releases a specific therapeutic agent which complements the wound healing cycle at a specific time point. For example, upon initial implantation of a medical device, it may be useful to release a therapeutic which stimulates neutrophils and macrophages, such as colony stimulating factors (CSFs). At a later time point, a second degradation zone may degrade, releasing an anti-inflammatory/pro-regenerative agent such as interleukin 10 (IL-10) to assist with minimizing chronic inflammation. At a third time point, a third degradation zone may degrade, releasing a bioactive agent such as bone morphogenic proteins (BMPs) which may signal for example, osteoblasts, in the case of the implant being an orthopedic repair device. Additionally, it should be known that implants according to the present disclosure are not limited to two or three degradation zones, and more than three degradation zones/mechanisms are also contemplated. Suitable bioactive agents which may be incorporated into devices of the present disclosure are listed below.

It should be noted that degradation zones according to the present disclosure may comprise or occupy varying volumes of the implant. For example, a first degradation zone may occupy from about 1/10 of the total implant volume to about 9/10 of the total implant volume. Conversely, the remaining degradation zone(s) may comprise the remainder of the implant. In another example, in the embodiment illustrated in FIGS. 1A and 1B, the distal portion 4 may occupy from about 1/10 of the total implant volume to about 9/10 of the total implant volume. The remaining proximal portion 6 may comprise the remainder of the implant volume.

The degradation rates of certain embodiments of the present disclosure may be altered by providing different materials or different compositions, copolymers and the like. For example, the bone anchor of FIG. 1A may be manufactured such that the distal portion 4 comprises a lactide/glycolide copolymer at a ratio of 70:30, while the proximal portion 6 may comprise a lactide/glycolide copolymer at a ratio of 85:15. In other embodiments having three degradation zones (e.g., FIG. 1B), the distal portion 4' may comprise a lactide/glycolide copolymer at a ratio of 70:30, an intermediate portion 5 may comprise a lactide/glycolide copolymer at a ratio of 85:15 and a proximal portion 6' including a lactide/glycolide copolymer at a ratio of 100:0. It should be understood that various polymers may be used in combination with each other, for example a dioxanone polymer may comprise a first degradable portion while collagen may comprise a second portion. It should also be noted that different materials may be combined to alter the degradation rates, for example, a degradable polymer may comprise a first degradable portion while a degradable metal alloy may comprise a second degradable portion. Various materials and compositions described above may be combined to create an implant having at least two degradation zones. Alternatively, different materials and compositions may yield similar degradation rates and mechanisms.

One skilled in the art can alter the degradation mechanism of the implant (as a whole or alternatively, various degradation zones) by changing parameters including but not limited to polymer composition and chemistry, density, morphology, crystal structure, solubility, thermal properties, molecular weight, size, porosity and pore size, wettability and processing parameters. It is within the purview of one skilled in the art to alter the processing of the implant to control the various parameters listed above including, but not limited to, polymer crystallinity and morphology, density, molecular weight, porosity and pore size. In general, the implant can be tailored to allow cells to proliferate and subsequent tissue ingrowth while the different degradation zones degrade over time.

Degradation rates or profiles may also be altered using different degradation mechanisms. For example, a polymer composition which undergoes bulk erosion may have a different degradation profile than a polymer composition (same or different) whose degradation mechanism is surface erosion. Bulk erosion occurs when the rate of water penetration into the implant exceeds the rate at which the polymer is transformed into a water-soluble material. As a result of water uptake, the bulk erosion process occurs throughout the entire volume of the implant. (Biomaterials Science, pp 123-125, Second Edition, Elsevier Academic Press 2004). Typically, hydrophilic polymers lend themselves to bulk erosion, although in certain embodiments, lactones (being hydrophobic) lend themselves to bulk erosion. Alternatively, surface erosion may occur in which the bioerosion process is limited to the surface of the device, hence the device gradually becomes thinner over time while maintaining its structural integrity over a longer period of time.

In some embodiments, at least one of the degradation zones may comprise a surface eroding polymer while another degradation zone may comprise a bulk eroding polymer. In certain embodiments, it may be advantageous to tailor the strength loss to correspond to the wound healing cycle. One way to control the strength loss may be in choosing to utilize a surface eroding polymer or a bulk eroding polymer. For example, in the bone anchor illustrated in FIG. 2A, it may be advantageous for the outer-most concentric zone to comprise a surface eroding polymer such as, for example, polyorthoester. This may enable the incorporation of tissue into the external portion of the device (while the outer portion surface erodes), providing a more stable implant throughout the wound healing cycle. Alternatively, the inner concentric portion (FIG. 2A) may comprise a bulk eroding polymer, such as, for example a lactide/glycolide copolymer, which enables the implant to maintain higher strength, stabilizing the overall implant and eyelet. It should be understood that various embodiments described herein may comprise combinations of surface eroding and bulk eroding polymers.

In another embodiment, the implant may comprise a fixation device including at least two homogeneous degradation zones. The term homogeneous as used herein means a composition which is unreinforced (with fillers/particulates), having a similar or consistent composition throughout the bulk material. Conversely, a heterogeneous implant may include polymers which have ceramic fillers (e.g., hydroxy apatite or tricalcium phosphate). Some embodiments of the present disclosure do not necessitate a ceramic filler, as the composite implants disclosed herein are of sufficient strength and rigidity to withstand forces associated with driving fixation devices into tissue. For example, implants may comprise suitable materials listed below in which at least two of the degradation zones are entirely polymers.

Alternatively, polymer crystallinity may be used to control the degradation rates of certain degradable polymers. In some polymers, changes in polymer morphology lead to changes in hydration and hydrolysis. Polymers which are highly crystalline, having a highly organized structure with tightly packed polymer chains may be more resistant to hydrolysis than a highly amorphous polymer. For example, poly(lactic acid) (PLA), exists in four morphologically distinct polymers, poly(D-lactide) (D-PLA), poly(L-lactide) (L-PLA), poly(D,L-lactide) (D,L-PLA) and meso poly(L-lactide) (meso-PLA). As an amorphous polymer, D,L-PLA is more hydrophilic, and therefore may lend itself to drug delivery type applications. Alternatively, semicrystalline L-PLA is preferred for use in applications which require higher strength and increased toughness, therefore, L-PLA may be preferred in certain applications. Polymer morphology may be controlled by controlling different processing methods and parameters to yield a desired morphology with a desired degradation rate. Suitable polymers include those listed below.

In certain embodiments of the present disclosure, degradation zones may be separated by an interface, while other embodiments of the present disclosure, degradation zones may be delineated by a gradual transition or an interphase. The term "interface" as used herein means a surface forming a common boundary between two regions, in this case between two degradation zones. The interface is a sharp transition from one degradation zone to another. The term "interphase" as used herein means generally the region between the bulk characteristics of the degradation zones. An interphase is a gradual transition or gradient transition from one degradation zone to another. For example, in FIG. 1, the distal degradation zone (bulk region) may comprise a lactide/glycolide ratio of about 82:18, while the proximal portion (bulk region) may comprise a ratio of about 90:10. The interphase, separating the proximal degradation zone from the distal degradation zone, may comprise a gradient transition of which the ratio of lactide/glycolide is somewhere between about 82:18 to about 90:10. In other words, the interphase region closer to the distal portion may comprise less lactide (closer to 82%) while the interphase region closer to the distal portion may comprise more lactide (closer to 90%). In another example, the implant may comprise an interphase in which the bulk porosity or bulk crystallinity undergoes a gradual transition, for example, from an inner concentric portion to an outer concentric portion of the implant. It should be understood that other embodiments according to the present disclosure may comprise an interphase or interface and the above description is not limited to the figures shown and described.

Additional compositions for different degradation zones or portions which may be useful in certain embodiments of the present disclosure are summarized in Table 1 below.

TABLE 1

| | Lactide/Glycolide Ratio | | |
|---|---|---|---|
| Example | Zone 1 | Zone 2 | Zone 3 |
| I | 70/30 | 85/15 | 100/0 |
| II | 82/18 | 85/15 | 90/10 |
| III | 85/15 | 90/10 | 100/0 |
| IV | 90/10 | 95/5 | 100/0 |

Altering the porosity of the implant may be another method to control the tissue ingrowth into and the degradation of various portions of the implant. Porous implants may have an open cell structure where the pores are connected to each other, forming an interconnected network. Conversely, implants of the present disclosure may be closed cell foams where the pores are not interconnected. Closed cell devices are generally denser and have a higher compressive strength. These may also be in the form of a foam or sponge-like material.

In certain embodiments, porous implants of the present disclosure can be manufactured using various processes within the purview of those skilled in the art. For example, foams can be manufactured though standard lyophilization (freeze drying) techniques, solvent casting and particulate leaching, compression molding, phase separation, gas foaming (e.g., internal blowing agents such as $CO_2$), or through the use of a porogen (e.g., salt particles). In certain embodiments, foams which are used as tissue scaffolds can also be created through computer aided design techniques including solid freeform fabrication (SFF), stereolithography, and the like.

Implants of the present disclosure may comprise biodegradable polymers including but not limited to polymers such as those made from polyesters such as lactide, glycolide, caprolactone, and valerolactone; poly carbonates (e.g., trimethylene carbonates, tetramethylene carbonates, tyrosine carbonates, polyimide carbonates, polyimino carbonates such as poly (bisphenol A-iminocarbonate) and poly(hydroquinone-iminocarbonate), and the like); dioxanones (e.g., 1,4-dioxanone); dioxepanones (e.g., 1,4-dioxepan-2-one and 1,5-dioxepan-2-one); ethylene glycol; ethylene oxide; esteramides; γ-hydroxyvalerate; β-hydroxypropionate; alpha-hydroxy acid; polyhydroxybuterates; poly(ortho esters); polyhydroxy alkanoates; polyurethanes; polyphosphazenes; poly(propylene fumarate); polyanhydrides; polyamines; polyester anhydrides; polymer drugs (e.g., polydiflunisol, polyaspirin, and protein therapeutics); biologically modified (e.g., protein, peptide) degradable polymers; and copolymers and combinations thereof.

Suitable natural biodegradable polymers include collagen; poly(amino acids); polysaccharides such as cellulose (including carboxymethyl cellulose), dextran, chitin, chitosan, alginate, hyaluronic acid, and glycosaminoglycans; fibrin and fibrinogen; hyaluronic acid; gut; copolymers and combinations thereof. Collagen as used herein includes natural collagen such as animal derived collagen, gelatinized collagen, or synthetic collagen such as human or bacterial recombinant collagen.

Certain embodiments may include suitable biodegradable ceramics such as alpha-tricalcium phosphate (alpha-TCP), beta-tricalcium phosphate (beta-TCP), hydroxyapatite, and combinations thereof.

Suitable biodegradable metal alloys include magnesium alloys and manganese alloys.

In some embodiments, hydrogels may comprise at least one of the degradation zones. Swellable materials may provide better anchoring and a more conformed fit into the tissue defect. Suitable swellable materials include but are not limited to degradable or modified polymers/copolymers including HEMA, vinyl pyrrolidone, acrylic acid, phosphorylcholine functional acrylates and methacrylates, hydroxymates, vinyl alcohol, and/or any other biocompatible vinyl monomers or polymers and combinations thereof. The above materials may be prepared by methods known to those skilled in the art including the use of a degradable crosslinker.

Methods to make implants of the present disclosure include injection molding with multiple injection points each being fed with different resin compositions. In other embodiments, sequential molding of resins can be done in which portions with faster degradation rates can be overmolded on portions which have slower degradation rates. Another alternate method of making implants of the present disclosure includes selective annealing of at least one of the compositions, yielding different crystal morphologies (e.g., crystalline versus amorphous regions and crystal size) which may alter degradation rates and degradation mechanisms (bulk versus surface erosion).

Alternatively, certain embodiments of the present disclosure can be reinforced with various materials such as films, woven, nonwoven, knitted or braided textile structures such as mesh. These reinforcements can be utilized to modify the degradation profile, to mechanically reinforce the implant, or as a carrier for controlled release of a bioactive agent.

Additionally, any part of the implant may include biologically acceptable additives such as plasticizers, antioxidants, dyes, image-enhancing agents, dilutants, bioactive agents such as pharmaceutical and medicinal agents, and combinations thereof which can be coated on the device or impregnated within the polymer, ceramic or metal alloy.

Medicinal agents which may be incorporated into the implant include antimicrobial agents, anti-virals, anti-fungals, and the like. Antimicrobial agents as used herein is defined by an agent which by itself or through assisting the body (immune system) helps the body destroy or resist microorganisms which may be pathogenic (disease causing). The term "antimicrobial agent" includes antibiotics, quorum sensing blockers, surfactants, metal ions, antimicrobial proteins and peptides, antimicrobial polysaccharides, antiseptics, disinfectants, anti-virals, anti-fungals, quorum sensing blockers, and combinations thereof. Examples of suitable antiseptics and disinfectants which may be combined with the present disclosure include hexachlorophene, cationic biguanides like chlorohexadine and cyclohexidine, iodine and iodophores like povidone-iodine, halo-substituted phenolic compounds like PCMX (e.g., p-chloro-m-xylenon) and triclosan (e.g., 2,4,4'-trichloro-2'hydroxy-diphenylether), furan medical preparations like nitrofurantoin and nitrofurazone, methanamine, aldehydes like gluteraldehyde and formaldehyde, alcohols, combinations thereof, and the like. In some embodiments, at least one of the antimicrobial agents may be an antiseptic, such as triclosan.

Classes of antibiotics that can be combined with the present disclosure include tetracyclines like minocycline, rifamycins like rifampin, macrolides like erythromycin, penicillins like nafcillin, cephalosporins like cefazolon, beta-lactam antibiotics like imipenen and aztreonam, aminoglycosides like gentamicin and TOBRAMYCIN®, chloramphenicol, sulfonamides like sulfamethoxazole, glycopeptides like vancomycin, quilones like ciproflaxin, fusidic acid, trimethoprim, metronidazole, clindamycin, mupirocin, polyenes like amphotericin B, azoles like fluconazole, and beta-lactam inhibitors like sublactam. Other antimicrobials which may be added include, for example antimicrobial peptides and/or proteins, antimicrobial polysaccharides, quorum sensing blockers (e.g., brominated furanones), antivirals, metal ions such as ionic silver and ionic silver glass, surfactants, chemotherapeutic drug, telomerase inhibitors, other cyclic monomers including 5-cyclic monomers, mitoxantrone, and the like.

In some embodiments, suitable bioactive agents which may be used include colorants, dyes, preservatives, protein and peptide preparations, protein therapeutics, polysaccharides such as hyaluronic acid, lectins, lipids, probiotics, angiogenic agents, anti-thrombotics, anti-clotting agents, clotting agents, analgesics, anesthetics, wound repair agents, chemotherapeutics, biologics, anti-inflammatory agents, anti-proliferatives, diagnostic agents, antipyretic, antiphlogistic and analgesic agents, vasodilators, antihypertensive and antiarrhythmic agents, hypotensive agents, antitussive agents, antineoplastics, local anesthetics, hormone preparations, antiasthmatic and antiallergic agents, antihistaminics, anticoagulants, antispasmodics, cerebral circulation and metabolism improvers, antidepressant and antianxiety agents, vitamin D preparations, hypoglycemic agents, anti-ulcer agents, hypnotics, antibiotics, antifungal agents, sedative agents, bronchodilator agents, antiviral agents, dysuric agents, brominated or halogenated furanones, and the like. In embodiments, polymer drugs, e.g., polymeric forms of such compounds for example, polymeric antibiotics, polymeric antiseptics, polymeric chemotherapeutics, polymeric anti-proliferatives, polymeric antiseptics, polymeric non-steroidal anti-inflammatory drugs (NSAIDS), and the like may be utilized and combinations thereof.

In certain embodiments, implants of the present disclosure may contain suitable medicinal agents such as viruses and cells, peptides, polypeptides and proteins, analogs, muteins, and active fragments thereof, such as immunoglobulins, antibodies (monoclonal and polyclonal), cytokines (e.g., lymphokines, monokines, chemokines), blood clotting factors, hemopoietic factors, interleukins (IL-2, IL-3, IL-4, IL-6), interferons (β-IFN, α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.) hormones and hormone analogs (e.g., growth hormone), vaccines (e.g., tumoral, bacterial and viral antigens), somatostatin, antigens, blood coagulation factors, growth factors, protein inhibitors, protein antagonists, and protein agonists, nucleic acids such as antisense molecules, DNA, RNA, oligonucleotides, polynucleotides and ribozymes and combinations thereof. It should be understood that the degradation mechanisms of implants according to the present disclosure may be tailored to provide specific release rates, wherein the degradation of certain materials may correspond to an elution or release of a bioactive agent.

Methods for combining the above mentioned bioactive agents with materials of the present disclosure are within the purview of those skilled in the art and include, but are not limited to mixing, blending, compounding, spraying, wicking, solvent evaporating, dipping, brushing, vapor deposition, coextrusion, capillary wicking, film casting, molding and the like. Additionally, solvents may be used to incorporate various agents into the device. Suitable solvents include but are not limited to polar and non-polar solvents such as alcohols, e.g., methanol, ethanol, propanol, chlorinated hydrocarbons (such as methylene chloride, chloroform, 1,2-dichloro-ethane), and aliphatic hydrocarbons such as hexane, heptene, and ethyl acetate.

Bioactive agents incorporated into devices of the present disclosure may have various release profiles including but not limited to zero order, first order, second order release profiles and combinations thereof. It is also within the purview of one skilled in the art to modify materials to be more hydrophobic or hydrophilic to achieve desired bioactive agent release results. As previously mentioned, bioactive agents and materials may both be altered to achieve specific release mechanisms to correspond with the integration of the implant into tissue.

Once the implant is constructed, it can be sterilized by any means within the purview of those skilled in the art including but not limited to ethylene oxide, electron beam (e-beam), gamma irradiation, autoclaving, plasma sterilization and the like.

As used herein, the term "tissue" includes, but is not limited to, tissues such as skin, fat, fascia, bones, muscles, tendons, ligaments, organs, nerves, and blood vessels. Also orthopedic devices as used herein includes devices which may be use in exemplary bones such as bones of the arms, legs, hands/feet, ankles, pelvic bones, cranial bones, spinal bones and vertebrae, ribs, clavicles and the like.

Figure 4:
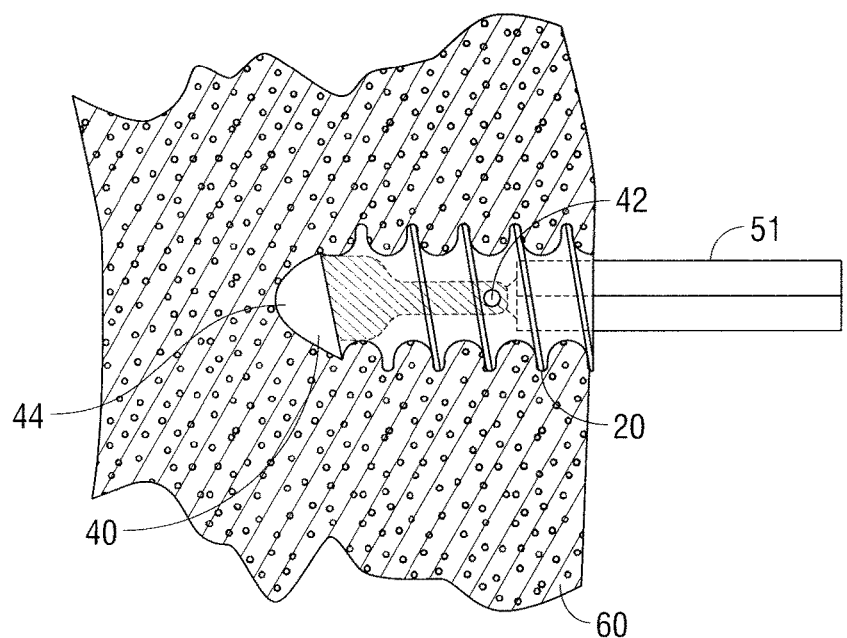
FIG. 4 shows a cross-sectional view of a bone screw of the present disclosure being inserted by an external driver into a bone mass according to the present disclosure.
Figure 5:
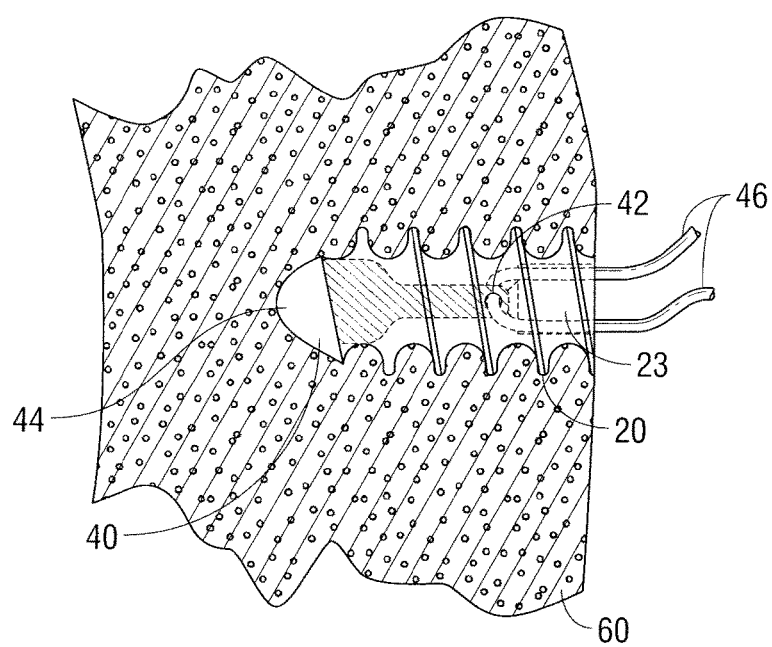
FIG. 5 shows a cross-sectional view of the bone screw and bone mass of FIG. 5, and further showing the free ends of suture threads extending therefrom.

Turning now to FIGS. 4 and 5, the bone screw 20 from FIG. 2A-2B is shown anchored into bone 60. The proximal end of the bone screw 20 has a hexagonal cross-section 52 which corresponds to a driver 51 which mates therewith, rotating the bone screw 20. As the driver 51 is inserted into the proximal end of the bone screw 20, it is driven into the bone 60. The suture threads 46 are also shown extending proximally from the bone screw axial passageway 23. The external driver 51 may be configured to allow the suture threads 46 to be retained within the driver while the bone screw 20 is driven into the bone. It should be understood that various embodiments of the present disclosure may be inserted into tissue in a similar manner and this example is not limited to embodiments illustrated herein.

It should be noted that the present disclosure is not limited to orthopedic repair devices including but not limited to nucleus repair devices, artificial meniscus, meniscal repair devices and fixation devices including but not limited to spinal fixation devices, fracture plates, wires, pins, screws (interference and bone), anchors, intramedullary devices, artificial ligaments, artificial tendons, cartilage implants/scaffolds, rotator cuff patches/grafts, and bone tendon grafts; and soft tissue repair devices including but not limited to sutures, buttresses, tacks, meshes, pledgets, plugs, anastomotic closure, anastomotic connection devices (e.g., sheaths), tissue patches and scaffolds.

While the above description contains many specifics, these specifics should not be construed as limitations on the scope of the disclosure, but merely as exemplifications of embodiments thereof. Those skilled in the art will envision many other possibilities within the scope and spirit of the disclosure as defined by the claims appended hereto.

What is claimed is:

1. A fixation device comprising at least two homogeneous degradation zones fabricated from polymeric materials that are not reinforced with ceramic or particulate fillers, the at least two homogeneous degradation zones including a first degradation zone having a first degradation rate and a second degradation zone having a second degradation rate that is different from the first degradation rate, and an interphase providing a gradient or gradual transition between the first degradation zone and the second degradation zone,
   wherein a region of the interphase closer to the first homogeneous degradation zone comprises more of the polymeric material of the first degradation zone than a region of the interphase closer to the second homogeneous degradation zone.

2. The fixation device according to claim 1, wherein at least one homogeneous degradation zone comprises a porous structure.

3. The fixation device according to claim 1, wherein the first degradation zone comprises more amorphous regions than the second degradation zone.

4. The fixation device according to claim 1, wherein the second degradation zone comprises more crystalline regions than the first degradation zone.

5. The fixation device according to claim 1, wherein at least one homogeneous degradation zone degrades by surface erosion.

6. The fixation device according to claim 1, wherein at least one homogeneous degradation zone degrades by bulk erosion.

7. The fixation device according to claim 1, further comprising a bioactive agent.

8. The fixation device according to claim 1, wherein at least one homogeneous degradation zone comprises a polymer drug.

9. The fixation device according to claim 1, wherein the degradation rate of at least one homogeneous degradation zone corresponds to an elution of at least one bioactive agent.

10. The fixation device according to claim 1, wherein at least one homogeneous degradation zone comprises materials selected from the group consisting of polyesters, polyester polyalkylene oxide copolymers, polyorthoesters, polyhydroxybutyrates, polyhydroxyalkanoates, polyanhydrides, polyamines, polycarbonates, copolymers and combinations thereof.

11. The fixation device according to claim 1, wherein a composition of the first degradation zone is different than a composition of the second degradation zone.

12. The fixation device according to claim 11, wherein a region of the interphase closer to the second homogeneous degradation zone comprises more of the polymeric material of the second degradation zone than a region of the interphase closer to the first homogeneous degradation zone.

13. The fixation device according to claim 1, wherein a composition of the first degradation zone is the same as a composition of the second degradation zone.

14. The fixation device according to claim 1, further comprising a third degradation zone having a third degradation rate.

15. A fixation device comprising at least two homogeneous degradation zones fabricated from polymeric materials that are not reinforced with ceramic or particulate fillers, the at least two homogeneous zones including a first degradation zone comprising a copolymer having a first ratio of monomers and a second degradation zone comprising the copolymer at a second ratio of monomers that is different from the first ratio of the first degradation zone, and an interphase providing a transition between the first degradation zone and the second degradation zone, wherein a region of the interphase proximal to the first homogeneous degradation zone comprises a ratio of monomers of the copolymer closer to the first ratio of the copolymer of the first degradation zone and a region of the interphase proximal to the second homogeneous degradation zone comprises a ratio of monomers of the copolymer closer to the second ratio of the second degradation zone.

* * * * *